(12) United States Patent
Wang et al.

(10) Patent No.: US 8,575,573 B2
(45) Date of Patent: Nov. 5, 2013

(54) STRUCTURE FOR DISCHARGING EXTREME ULTRAVIOLET MASK

(75) Inventors: You-Jin Wang, Milpitas, CA (US); Chiyan Kuan, Danville, CA (US); Chung-Shih Pan, Palo Alto, CA (US)

(73) Assignee: Hermes Microvision, Inc., Hsinchu (TW)

( * ) Notice: Subject to any disclaimer, the term of this patent is extended or adjusted under 35 U.S.C. 154(b) by 0 days.

(21) Appl. No.: 13/112,536

(22) Filed: May 20, 2011

(65) Prior Publication Data

US 2012/0292509 A1 Nov. 22, 2012

(51) Int. Cl.
*A61N 5/00* (2006.01)

(52) U.S. Cl.
USPC ............ 250/492.1; 250/310; 430/5; 361/212; 361/220; 361/222

(58) Field of Classification Search
USPC ................. 250/306, 307, 308, 309, 310, 311; 430/5; 361/212, 220, 222
See application file for complete search history.

(56) References Cited

U.S. PATENT DOCUMENTS

| | | | | |
|---|---|---|---|---|
| 4,610,020 A * | 9/1986 | La Fiandra | ...................... | 378/35 |
| 5,608,773 A * | 3/1997 | Korenaga et al. | ................ | 378/34 |
| 5,671,123 A * | 9/1997 | Omori et al. | ................... | 361/737 |
| 6,172,738 B1 * | 1/2001 | Korenaga et al. | ................ | 355/53 |
| 6,906,305 B2 * | 6/2005 | Pease et al. | ................. | 250/208.1 |
| 7,834,982 B2 * | 11/2010 | Yamamoto | ...................... | 355/72 |
| 2001/0022652 A1 * | 9/2001 | van Schaik et al. | ............. | 355/53 |
| 2002/0047093 A1 * | 4/2002 | Son et al. | ...................... | 250/307 |
| 2002/0070340 A1 * | 6/2002 | Veneklasen et al. | .......... | 250/310 |
| 2002/0075469 A1 * | 6/2002 | Tanaka | .............................. | 355/72 |
| 2003/0162101 A1 * | 8/2003 | Heerens et al. | .................... | 430/5 |
| 2006/0292457 A1 * | 12/2006 | Meijer et al. | ....................... | 430/5 |
| 2007/0117028 A1 * | 5/2007 | Heerens et al. | .................... | 430/5 |
| 2008/0149830 A1 * | 6/2008 | Baek et al. | ..................... | 250/310 |
| 2009/0301917 A1 * | 12/2009 | Kolbow et al. | ................. | 206/454 |

* cited by examiner

*Primary Examiner* — Robert Kim
*Assistant Examiner* — Jason McCormack
(74) *Attorney, Agent, or Firm* — Muncy, Geissler, Olds & Lowe, PLLC

(57) ABSTRACT

A structure for discharging an extreme ultraviolet mask (EUV mask) is provided to discharge the EUV mask during the inspection by an electron beam inspection tool. The structure for discharging an EUV mask includes at least one grounding pin to contact conductive areas on the EUV mask, wherein the EUV mask may have further conductive layer on sidewalls or/and bottom. The inspection quality of the EUV mask is enhanced by using the electron beam inspection system because the accumulated charging on the EUU mask is grounded.

7 Claims, 20 Drawing Sheets

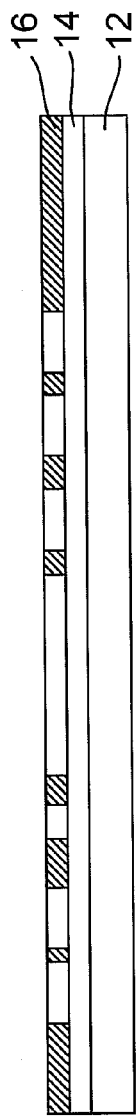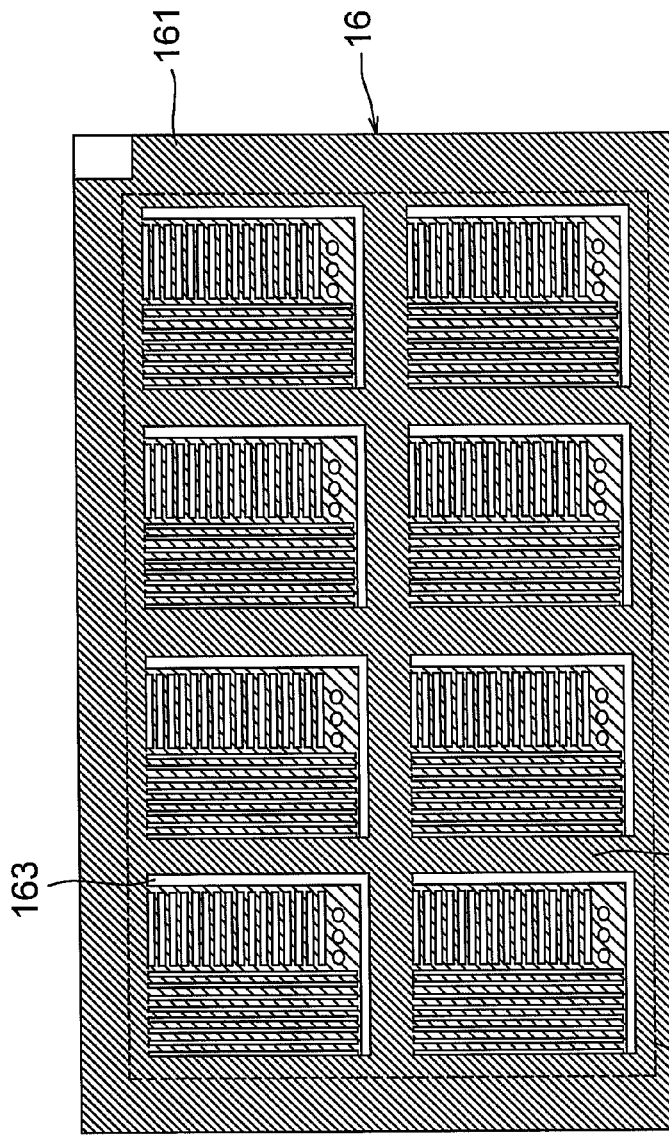

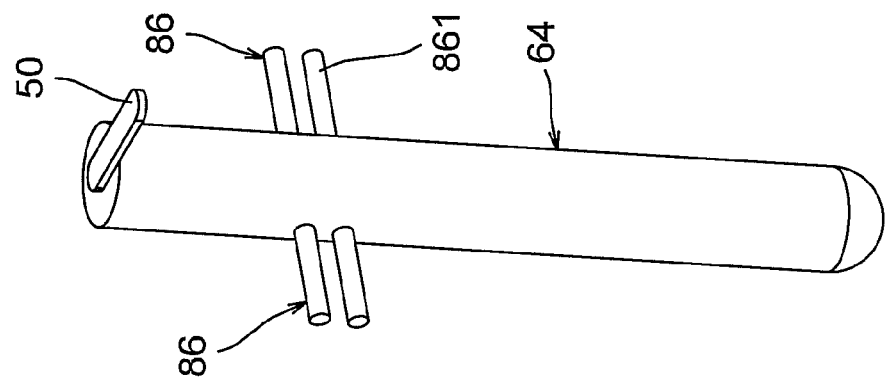
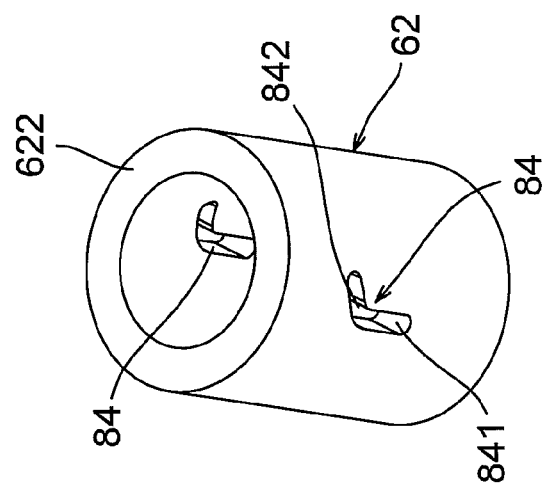
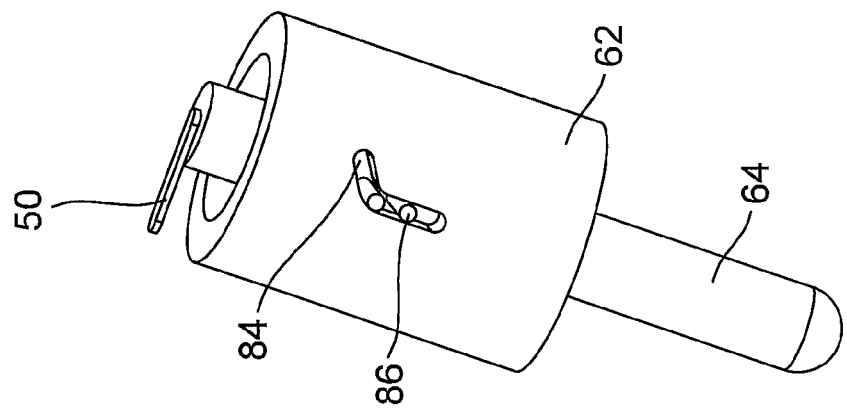

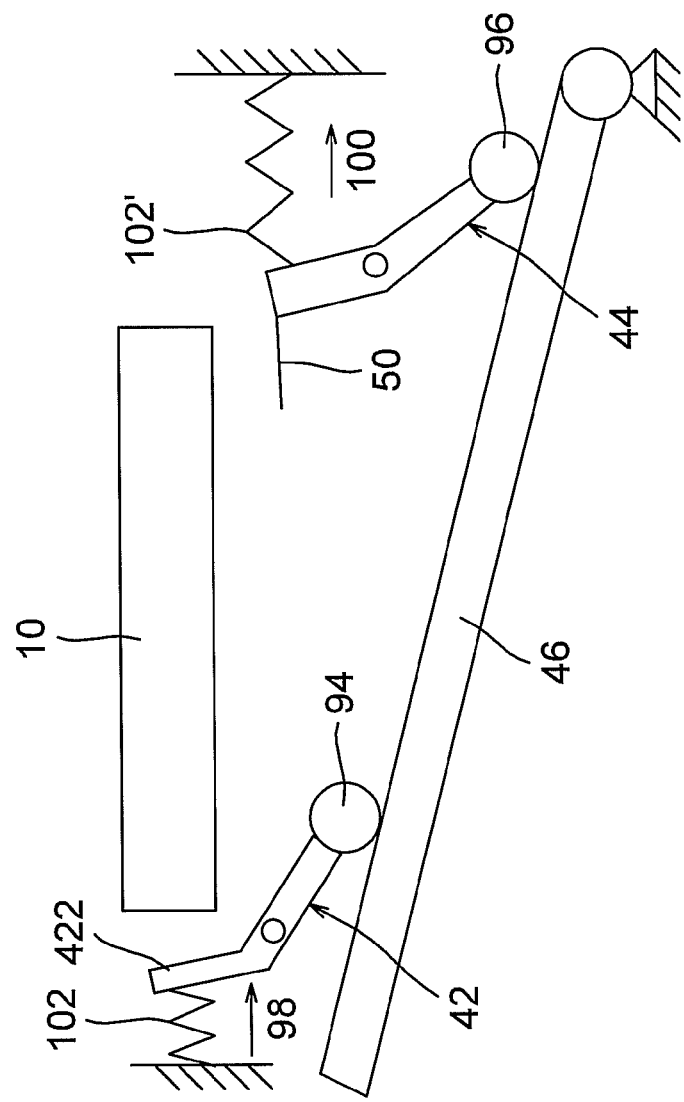

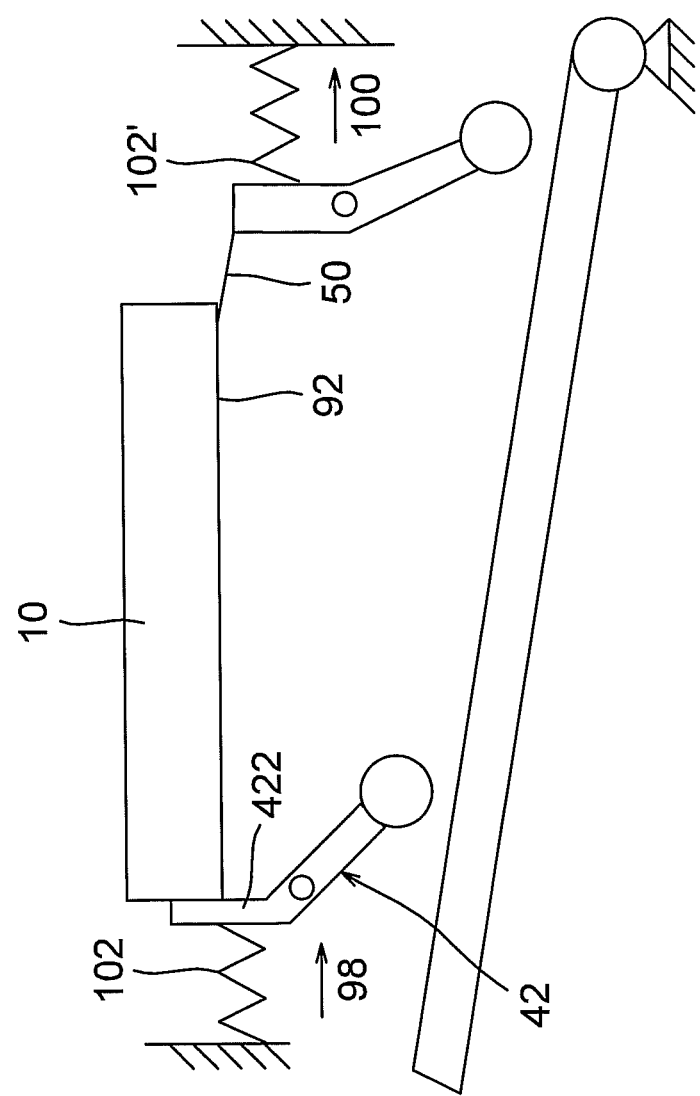

STRUCTURE FOR DISCHARGING EXTREME ULTRAVIOLET MASK

BACKGROUND OF THE INVENTION

1. Field of the Invention

The present invention relates to a discharging structure, and more especially, to a structure for discharging the extreme ultraviolet mask (EUV mask) during the EUV mask is inspected by the charged particle beam inspection system.

2. Background of the Related Art

Optical inspection of a mask is based on a comparison of the light signals in the patterned regions relative to the non-patterned regions. A high contrast is necessary in order to achieve sufficient sensitivity for defect detection. The transmissive masks used in DUV (deep Ultra Violet) lithography can be inspected without difficulty since the contrast between the opaque regions and the clear regions is high at UV/DUV wavelengths. However, it is difficult to inspect the reflective masks, the EUV mask for example, used in EUV lithography since not only the contrast between the absorber region and the mirror region is low at UV/DUV wavelengths, but also wavelength of the UV/DUV is too lengthy to inspect EUV mask.

Now, a charged particle beam inspection system, an electron beam (E-beam) inspection tool, accordingly, is developed to inspect the EUV mask. However, accumulated charging on EUV mask will induce inspection issue while the EUV mask is inspected by E-beam inspection tool. This issue will not happen to silicon wafer because silicon wafer can be grounded. Substrate of the EUV mask is dielectric, and can not be grounded.

SUMMARY OF THE INVENTION

In order to solve the foregoing problems, one object of this invention is to provide a structure to discharge the EUV mask during inspection by an E-beam inspection tool, so that non accumulated charging is on the EUV mask during E-beam inspecting to enhance the inspection quality.

Accordingly, one embodiment of the present invention provides a structure for discharging EUV mask including: means for conducting charge on an EUV mask in inspecting the EUV mask by using a charged particle beam inspection system; and a grounding pin to contact the means.

Another embodiment of the present invention provides a structure for discharging EUV mask including: at least a conductive layer on one side of an EUV mask; and a grounding pin to contact the conductive layer, so that charge on a reflective surface of the EUV mask is grounded through the conductive layer to the grounding pin.

Another embodiment of the present invention provides a structure for discharging EUV mask including: a first conductive layer on one side of an EUV mask; a second conductive layer on a surface opposite to a reflective surface of the EUV mask; and a grounding pin to contact the second conductive layer, so that charge on the reflective surface of the EUV mask is grounded through the second conductive layer to the grounding pin.

Another embodiment of the present invention provides an electron beam inspection system for inspecting an EUV mask including: an electron gun for providing electron beam; a lens for focusing the electron beam on the EUV mask; a detector for receiving signal electron emanating from the EUV mask; and means for discharging the EUV mask during the EUV mask is inspected.

BRIEF DESCRIPTION OF THE DRAWINGS

FIG. 1 illustrates a cross-sectional view of a configuration of an EUV mask;

FIG. 2 illustrates a vertical view of a configuration of an EUV mask;

FIG. 10a, FIG. 10b and FIG. 10c illustrates a third embodiment of the grounding pin controlling structure;

FIG. 12a and FIG. 12b illustrate the diagrams about the working status of the EUV mask and the grounding pin in accordance with the fourth embodiment of the present invention;

DETAILED DESCRIPTION OF THE INVENTION

Figure 3A:
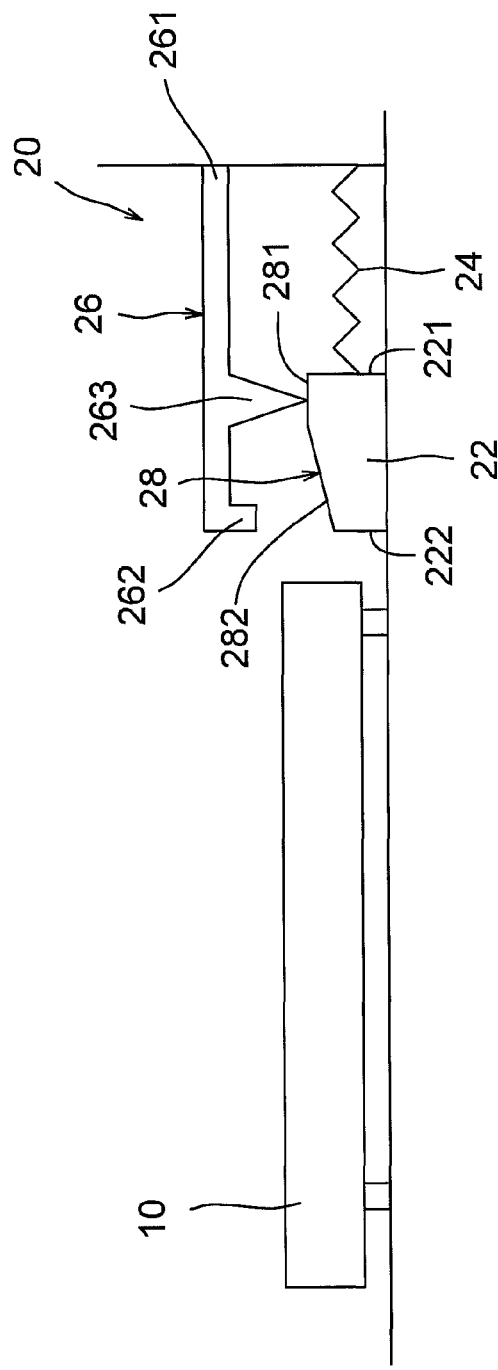
FIG. 3a and FIG. 3b illustrate the diagrams about the working status of the EUV mask and the grounding pin in accordance with the first embodiment of the present invention.

FIG. 1 illustrates a cross-sectional view of a configuration of an EUV mask. The EUV mask 10 includes a substrate 12, an EUV absorption layer 14 on the substrate 12 and a patterned reflective surface 16 formed on the absorption layer 14. Referring to FIG. 2 simultaneously, the patterned reflective surface 16 has a peripheral area 161 without any pattern and a middle area 162 with a plurality of pattern openings 163 thereon. A structure for discharging EUV mask includes: means for conducting charge on the EUV mask 10 in inspecting the EUV mask 10 by using a charged particle beam inspection system; and a grounding pin (shown in following diagrams) to contact the means. In one embodiment, the grounding pin is used to contact a portion of the peripheral area 161 of the patterned reflective surface 16, which is made of electrical conductive materials, or electrical semiconductive materials, and thereby grounds charges on the reflective surface 16 of the EUV mask 10.

Figure 3B:
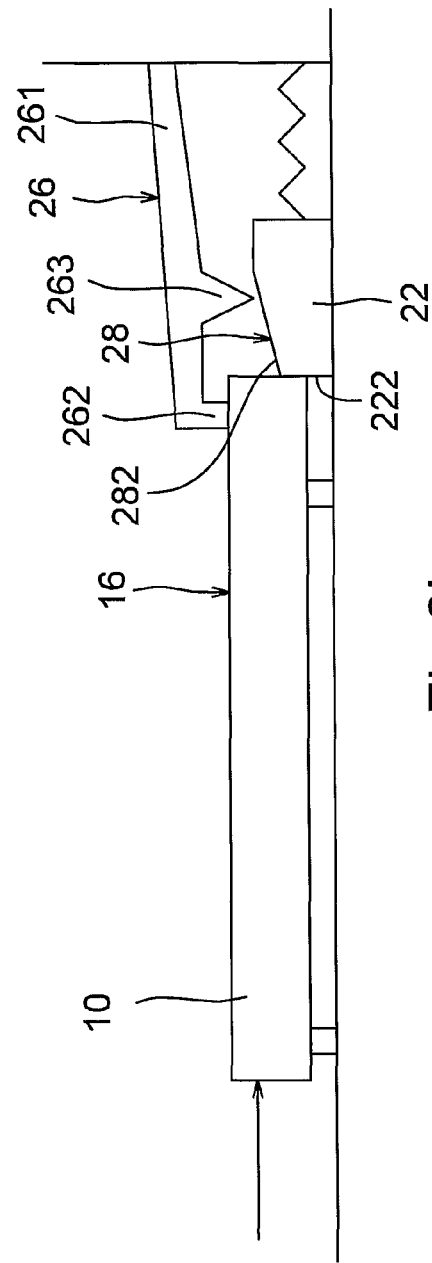

FIG. 3a and FIG. 3b illustrate the diagrams about the working of the EUV mask and the grounding pin in accordance with the first embodiment of the present invention. In the first embodiment, the structure 20 for discharging EUV mask further includes a slider 22, a spring 24 and an arm structure 26. The slider 22 has a top surface 28 divided into a flat area 281 and a downward-tilted area 282. One end of the spring 24 connects to a back side 221 of the slider 22 and the other end of the spring 24 is fixed. The arm structure 26 is above the slider 22 and the arm structure 26 includes a body 261, the grounding pin 262 on a front end of the body 261 and a prop 263 connecting to the body 261. As shown in FIG. 3a, when the EUV mask 10 is under the ungrounded status, the prop 263 of the arm structure 26 contact the flat area 281 of the slider 22 and the grounding pin 262 is far away from the EUV mask 10. When the EUV mask 10 moves toward a front side 222 of the slider 22 to contact and push the slider 22 back, as shown in FIG. 3b, the prop 263 moves along the top surface 28 of the slider 22 and then contacts the downward-tilted area 282, and therefore the body 261 of the arm structure 26 tilts and the grounding pin 262 contacts the reflective surface 16 of the EUV mask 10.

Figure 5:
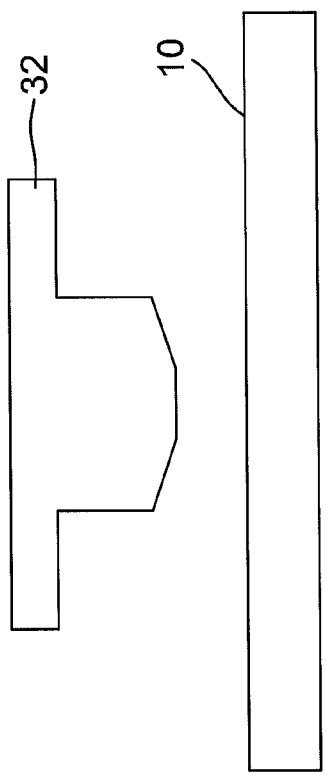
FIG. 5 illustrates a diagram about a configuration of the EUV mask and the electron gun.
Figure 4:
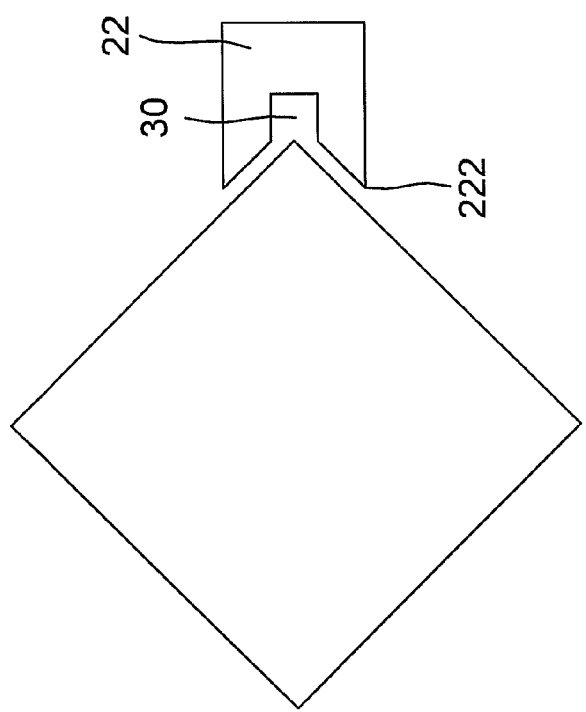
FIG. 4 illustrates a diagram about a configuration of the EUV mask and the slider.

As shown in FIG. 4, the slider 22 has a gap 30 on the front side 222 of the slider 22 for holding one corner of the EUV mask 10, so that the slider 22 may fix the EUV mask 10, as the EUV mask 10 contacts with the slider 22 during the EUV mask 10 is grounded by the grounding pin 262 (shown in FIG. 3a, FIG. 3b) and inspected by charged particle beam inspection system, in which the electron gun 32 for providing electron beam is above the EUV mask 10, as shown in FIG. 5.

Figure 6A:
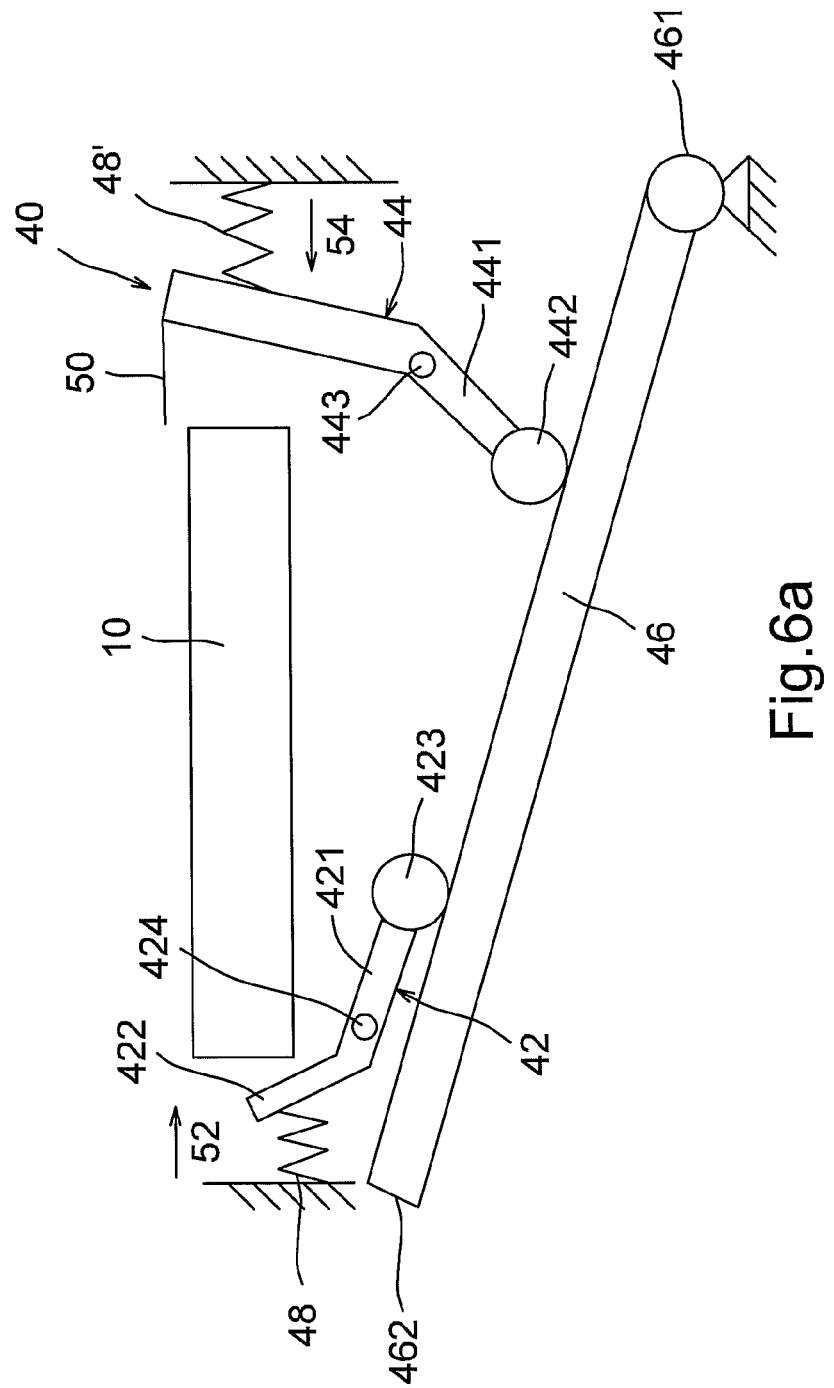
FIG. 6a and FIG. 6b illustrate the diagrams about the working status of the EUV mask and the grounding pin in accordance with the second embodiment of the present invention.
Figure 6B:
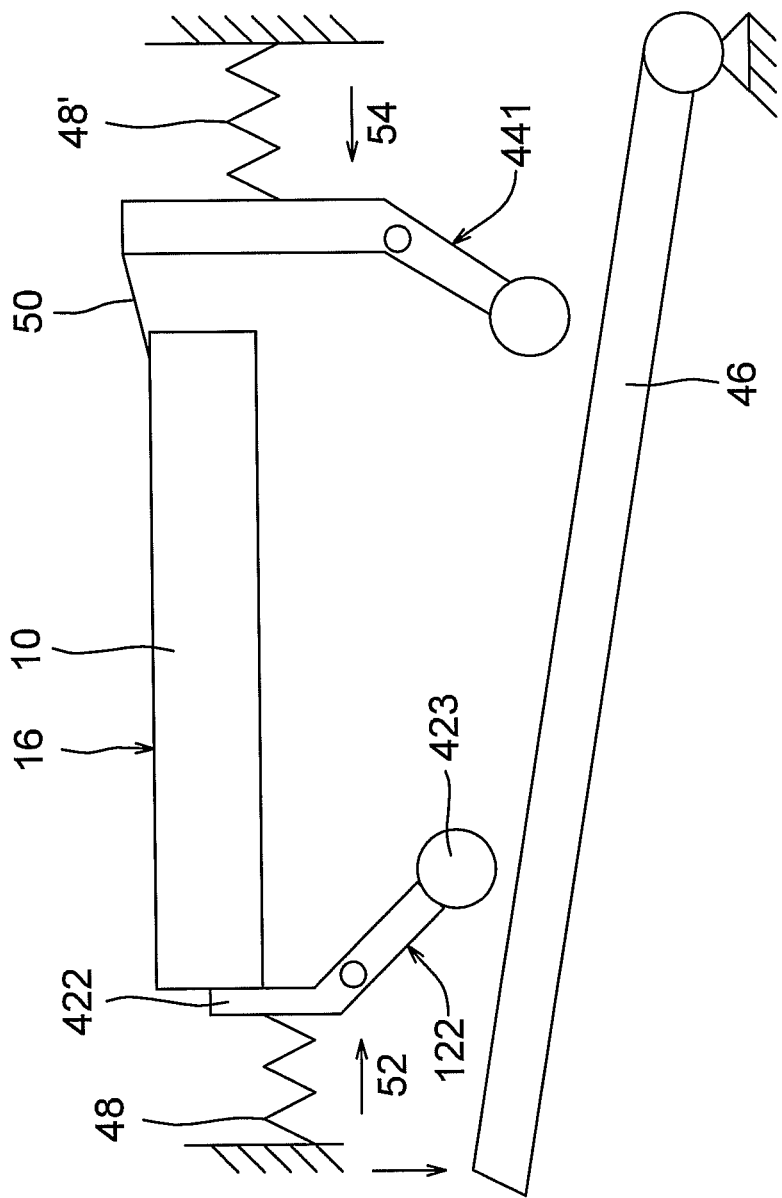

FIG. 6a and FIG. 6b illustrate the diagrams about the working status of the EUV mask and the grounding pin in accordance with the second embodiment of the present invention. In the second embodiment, as shown in FIG. 6a and FIG. 6b, the structure 40 for discharging EUV mask further includes a gripper unit 42, an arm structure 44, a reciprocating member 46 and two resilient members 48, 48'.

The gripper unit 42 includes a head portion 421, a base portion 422 and a first rolling member 423 set at a bottom end of the base portion 421. The gripper unit 42 is used for fixing the EUV mask 10 in place, for example but not limited to, being held tight or to be released, through rotation of the gripper unit 42 about a first pivot 424 substantially parallel with a first center axis of the first rolling member 423.

The arm structure 44 is configured near or opposite the gripper unit 42. The arm structure 44 includes a body 441, the grounding pin 50 on a top end of the body 441 and a second rolling member 442 set at a bottom end of the body 441. The grounding pin 50 may reciprocate to contact the EUV mask 10 and leave the EUV mask 10 through rotation of the body 441 about a second pivot 443 substantially parallel with a second center axis of the second rolling member 442.

The two resilient members are one first resilient member 48 and one second resilient member 48' each with one end being fixed, and respectively with the other ends being connected to head portion 422 of the gripper unit 42 and to the body 441 of the arm structure 44 for respectively providing a first force to the gripper unit 42 toward a first direction 52 and a second force to the body 441 of the arm structure 44 toward a second direction 54.

The reciprocating member 46 is configured for causing the first rolling member 423 and the second rolling member 442 to rotate. The reciprocating member 46 includes a fix end 461 and a mobile end 462 pivoting the fixed end 461. The first rolling member 423 and the second rolling member 442 may be in contact with reciprocating member 46 and roll freely on the surface of the reciprocating member 46. Here, the reciprocating member 46 is tilted by pushing up and pulling down the mobile end 462 of the reciprocating member 46 pivoting the fixed end 461 of the reciprocating member 46, which results in the first rolling member 423 and the second rolling member 442 rolling on the reciprocating member 46.

As shown in FIG. 6a, when the reciprocating member 46 works to make the first rolling member 423 to move substantially along the first direction 52 and the second rolling member 442 move substantially along the second direction 54, the head portion 422 of the gripper unit 42 moves toward the opposite direction of the first direction 52 and the grounding pin 50 moves toward the opposite direction of the second direction 54 so that the head portion 422 and the grounding pin 50 are led away from the EUV mask 10. As shown in FIG. 6b, when the reciprocating member 46 works to leave the first rolling member 423 and the second rolling member 442, the head portion 422 of the gripper unit 42 moves toward the first direction 52 by means of the first force of the first resilient member 48 and an upper portion of the arm structure 44 moves toward the second direction 54 by means of the second force of the second resilient member 48', so that the head portion 422 is therefore led toward the edge of the EUV mask 10 and in the end to abut against the EUV mask 10, and the grounding pin 50 contacts the reflective surface 16 of the EUV mask 10. Here, the head portion 422 of the gripper unit 42 is used to push tighter against the EUV mask 10 to hold it fixed in position during the EUV mask 10 is grounded by the grounding pin 50 and inspected by the charged particle beam inspection system.

Figure 7A:
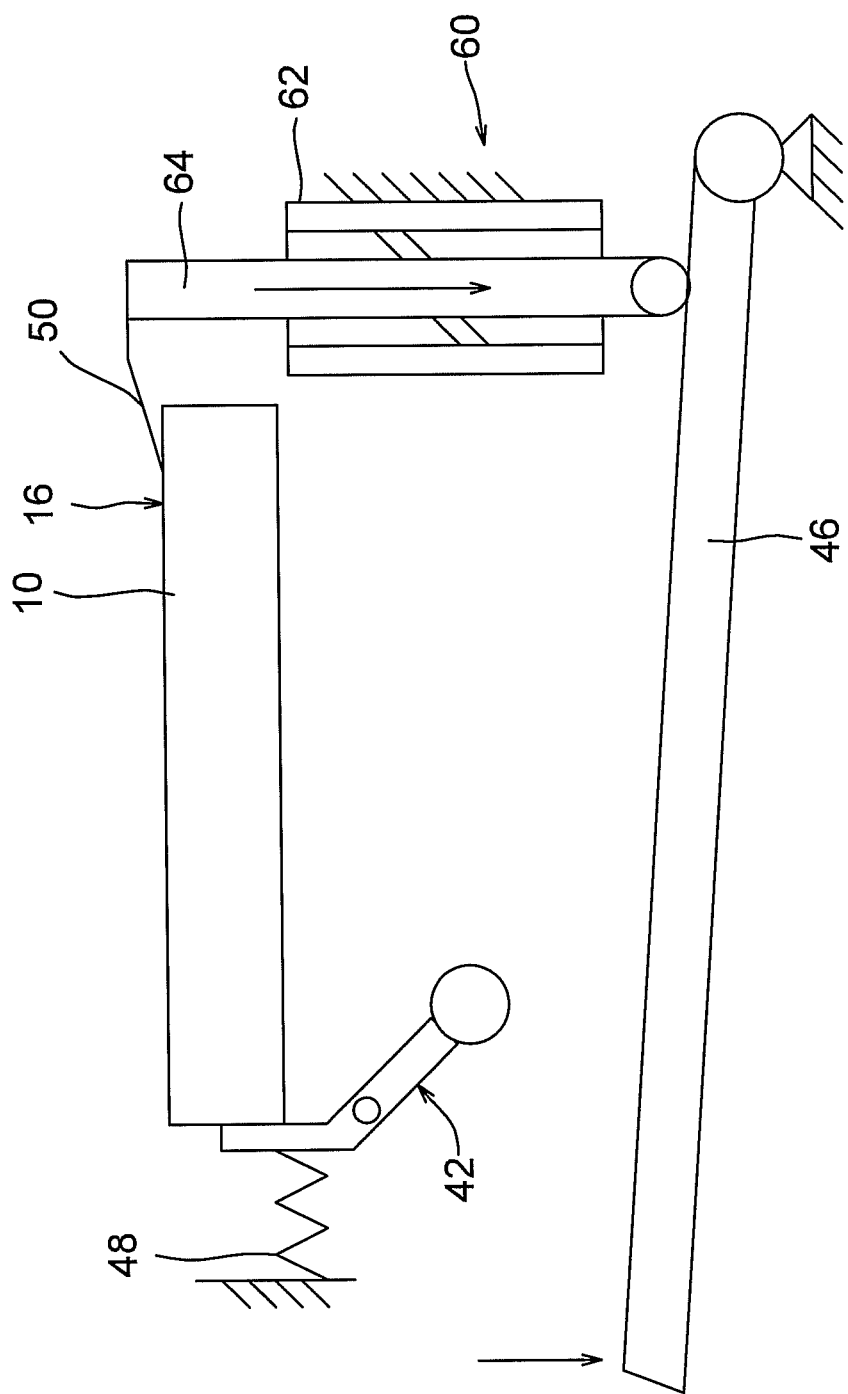
FIG. 7a and FIG. 7b illustrate the diagrams about the working status of the EUV mask and the grounding pin in accordance with the third embodiment of the present invention.
Figure 7B:
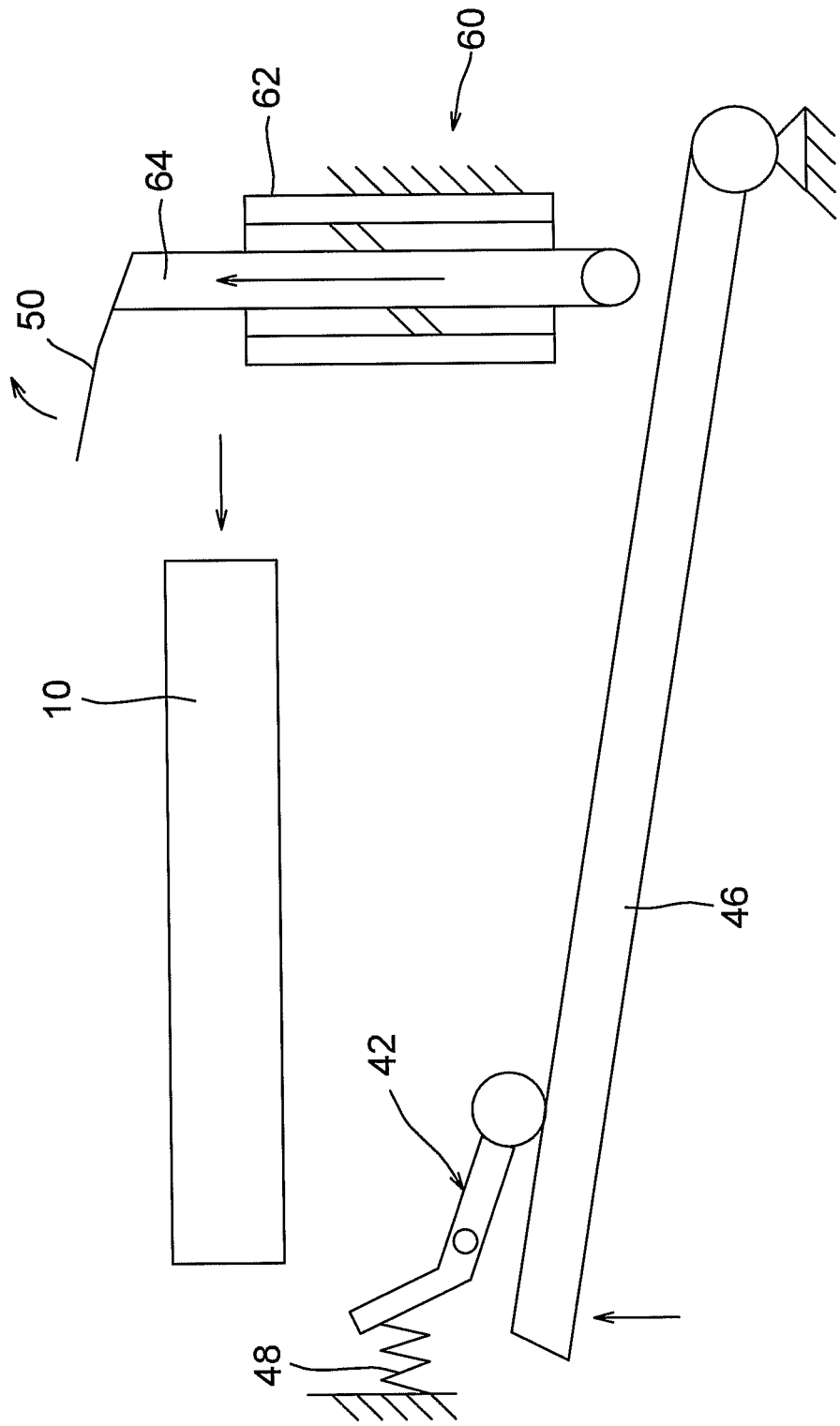

FIG. 7a and FIG. 7b illustrate the diagrams about the working status of the EUV mask and the grounding pin in accordance with the third embodiment of the present invention. In the third embodiment, the structure for discharging EUV mask further includes the foregoing gripper unit 42, the foregoing first resilient member 48, the foregoing reciprocating member 46 and a grounding pin controlling structure 60. Here, the structures, the connection relations and the operation of the gripper unit 42, the first resilient member 48 and the reciprocating member 46 are described in the second embodiment as shown in FIG. 6a and FIG. 6b, wherein the head portion 422 of the gripper unit 42 is used to push tighter against the EUV mask 10 to hold it fixed in position during the EUV mask 10 is grounded by the grounding pin 50. The grounding pin controlling structure 60 includes a hollow cylinder 62 and a column 64 passing through the hollow cylinder 62. A grounding pin 50 is arranged on a top surface of the column 64 and the position of the grounding pin 50 is changed by moving the column 64. As shown in FIG. 7a, when the gripper unit 42 pushes tighter against the EUV mask 10, the column 64 moves down and the grounding pin 50 contacts the reflective surface 16 of the EUV mask 10. As shown in FIG. 7b, when the gripper unit 42 releases the EUV mask 10, the column 62 moves up and the grounding pin 50 is far away from the EUV mask 10.

Figure 8:
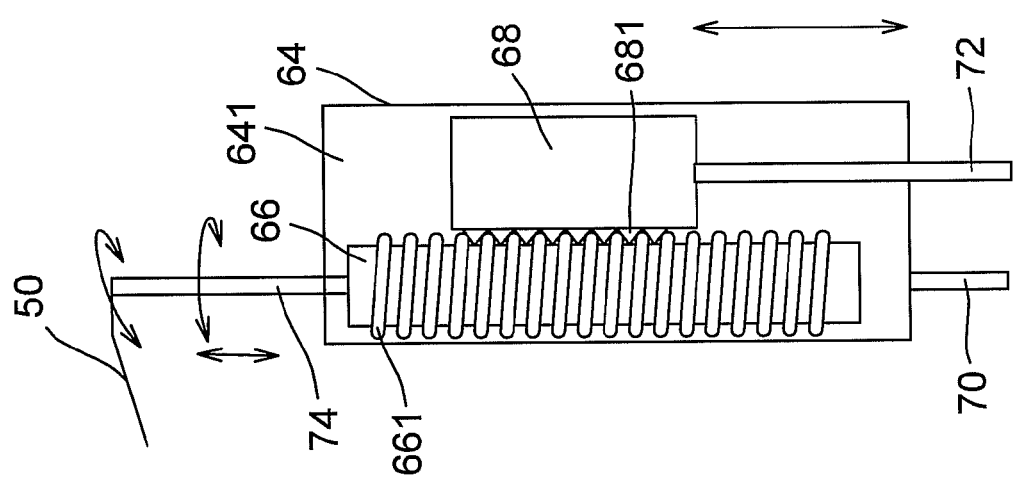
FIG. 8 illustrates a first embodiment of the grounding pin controlling structure.

In first embodiment of the grounding pin controlling structure, the grounding pin controlling structure 60 includes a hollow cylinder 62 and a column 64 passing through the hollow cylinder 62, wherein the column 64 has an interior room 641, as shown in FIG. 8. A first rod 66 with the spiral shells 661 on the outer surface and a second rod 68 with the sawtooth 681 on the outer surface are configured in the interior room 641, wherein the spiral shells 661 and the sawtooth 681 are engaged with each other. A first pushing shaft 70 is connected to the bottom of the column 64 and a second pushing shaft 72 is connected to the bottom of the second rod 68 and passes through the bottom of the column 64. One end of a connection rod 74 is connected to the top of the first rod 66, and another end of the connection rod 74 is connected with a grounding pin 50. During the inspection of the EUV mask 10, the column 64 moves down in relative to the hollow cylinder 62 (shown in FIG. 7*a*), so that the grounding pin 50 contacts the reflective surface 16 of the EUV mask 10 (shown in FIG. 7*a*). After the inspection of the EUV mask 10, the column 64 moves up continuously in relative to the hollow cylinder 62 (shown in FIG. 7*b*) so that the grounding pin 50 rise, wherein the second rod 72 also moves up to drive the first rod 66 to rotate with the sawtooth 681 engaging with the spiral shells 661, so that the grounding pin 50 may rise and deflect, simultaneously to be far away from the EUV mask.

Figure 9C:
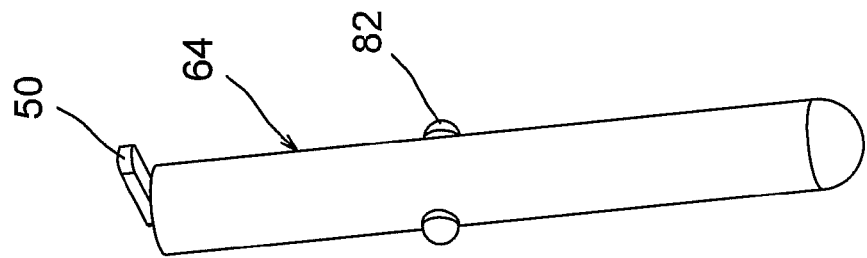
FIG. 9a, FIG. 9b and FIG. 9c illustrates a second embodiment of the grounding pin controlling structure.
Figure 9B:
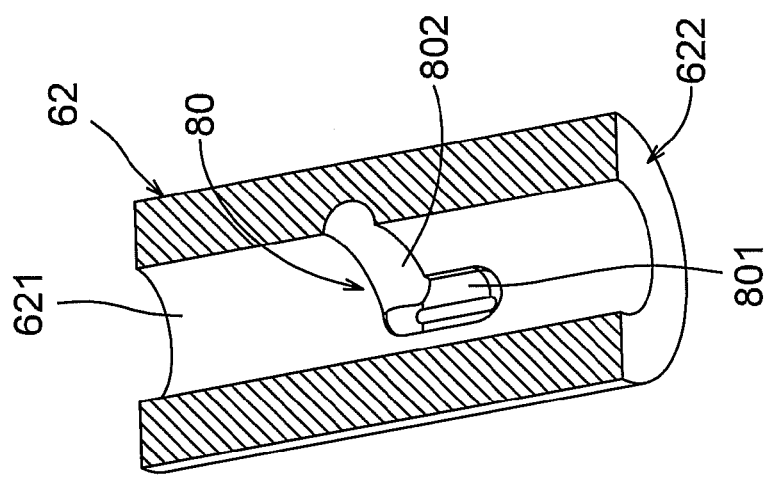
Figure 9A:
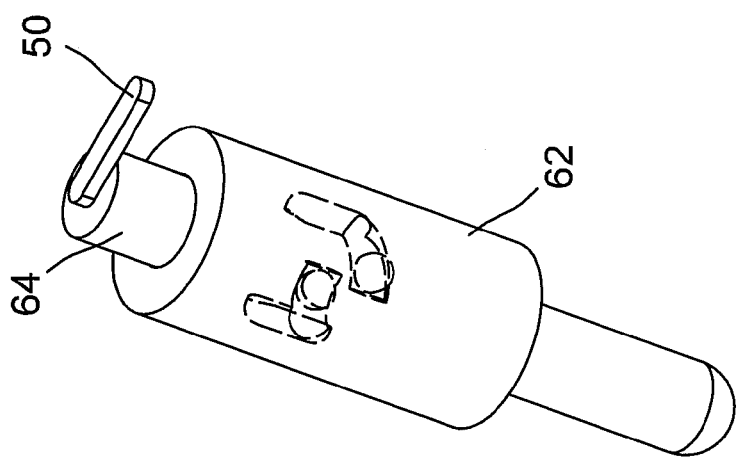

In second embodiment of the grounding pin controlling structure, as shown in FIG. 9*a*, the grounding pin controlling structure 60 includes a hollow cylinder 62 and a column 64 passing through the hollow cylinder 62. As shown in FIG. 9*b*, the hollow cylinder 62 has two opposite trenches 80 formed on an inner surface 621 of a side wall 622 of the hollow cylinder 62, wherein each trench 80 has a lengthwise ditch 801 and an upward-tilted ditch 802 connecting to a top end of the lengthwise ditch 801. Correspondingly, as shown in FIG. 9*c*, the column 64 has two opposite protrusions 82 on an outer surface of the column 64 and the protrusions 82 are respectively arranged within the opposite trenches 80, as shown in FIG. 9*a* to move along the lengthwise ditch 801 and the upward-tilted ditch 802. During the inspection of the EUV mask, the column 64 moves down in relative to the hollow cylinder 62 (shown in FIG. 7*a*), so that the grounding pin 50 contacts the reflective surface 16 of the EUV mask 10 (shown in FIG. 7*a*). After the inspection of the EUV mask 10, the column 64 moves up continuously in relative to the hollow cylinder 62, wherein the column 64 moves up straightly and then deflects as protrusions 82 moves along the lengthwise ditch 801 and then the upward-tilted ditch 802, so that the grounding pin 50 is far away from the EUV mask 10.

In third embodiment of the grounding pin controlling structure, as shown in FIG. 10*a*, the grounding pin controlling structure 60 includes a hollow cylinder 62 and a column 64 passing through the hollow cylinder 62. As shown in FIG. 10*b*, the hollow cylinder 62 has two opposite trenches 84 passing through a side wall 622 of the hollow cylinder 62, wherein each trench 84 has a lengthwise ditch 841 passing through the side wall 622 and a upward-tilted ditch 842 passing through the side wall 622 and connecting to a top end of the lengthwise ditch 841. Correspondingly, as shown in FIG. 10*c*, the column 64 has two opposite branch structures 86 including at least two horizontal rods 861 respectively, and the branch structures 86 are respectively arranged within the opposite trenches 84, as shown in FIG. 10*a*, to move along the lengthwise ditch 841 and the upward-tilted ditch 842. During the inspection of the EUV mask, the column 64 moves down in relative to the hollow cylinder 62 (shown in FIG. 7*a*), so that the grounding pin 50 contacts the reflective surface 16 of the EUV mask 10 (shown in FIG. 7*a*). After the inspection of the EUV mask 10, the column 64 moves up continuously in relative to the hollow cylinder 62, wherein the column 64 moves up straightly and then deflects as the branch structures 86 moves along the lengthwise ditch 841 and the upward-tilted ditch 842, so that the grounding pin 50 is far away the EUV mask 10.

Figure 11:
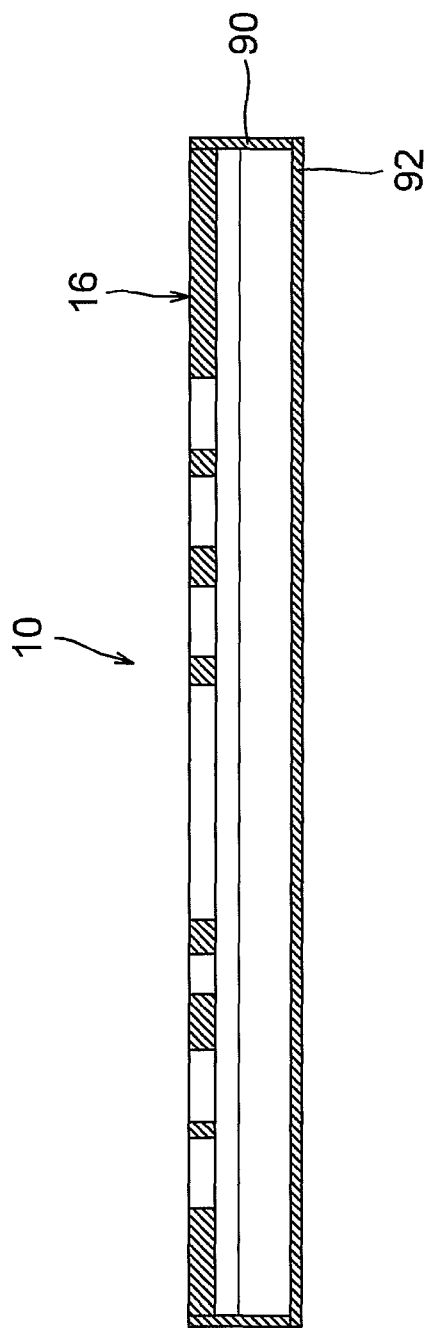
FIG. 11 illustrates a cross-sectional view of a configuration of another EUV mask.

In the foregoing embodiments, the grounding pin 50 is used to contact the reflective surface 16 which is formed on the top surface of the EUV mask 10. Nevertheless, the position that the grounding pin contacts with may be changed. As shown in FIG. 11, a first conductive layer 90 and a second conductive layer 92 may respectively be coated on the side of the EUV mask 10 and coated on the bottom surface, which is opposed to the reflective layer 16, of the EUV mask 10. The reflective surface 16, the first conductive layer 90 and the second conductive layer 92 are electrically connected, so that the foregoing grounding pin 50 may be used to contact the second conductive layer 92, so that charge on the reflective surface 16 of the EUV 10 mask is grounded through the first conductive layer 90 and the second conductive layer 92 to the grounding pin 50. The coated first conductive layer 90 and the second conductive layer 92 may be Al, Cr, Ti, alloy thereof, or non-metal such as carbon. The thickness of the first conductive layer 90 and the second conductive layer 92 may be 0.001 um to 1 mm.

Continuing the above description, the drive mechanism of the gripper unit described in the second embodiment of the present invention may be applied to the EUV mask with the first conductive layer and the second conductive layer. As shown in FIG. 12*a*, when the reciprocating member 46 works to make the third rolling member 94 to move substantially along the third direction 98 and the fourth rolling member 96 move substantially along the fourth direction 100, the head portion 422 of the gripper unit 42 moves toward the opposite direction of the third direction 98 and the grounding pin 50 moves toward the opposite direction of the fourth direction 100 so that the head portion 422 and the grounding pin 50 are led away from the EUV mask 10. As shown in FIG. 12*b*, when the reciprocating member 46 works to leave from the third rolling member 94 and the fourth rolling member 96, the head portion 422 of the gripper unit 42 moves toward the third direction 98 by means of the third force of the third resilient member 102 and an upper portion of the arm structure 44 moves toward the fourth direction 100 by means of the fourth force of the fourth resilient member 102' so that the head portion 422 is therefore led toward the edge of the EUV mask 10 and in the end to abut against the EUV mask 10, and the grounding pin 50 contacts the second conductive layer 92 of the EUV mask 10 to discharge the charge on the reflective surface 16 of the EUV mask 10.

Figure 13A:
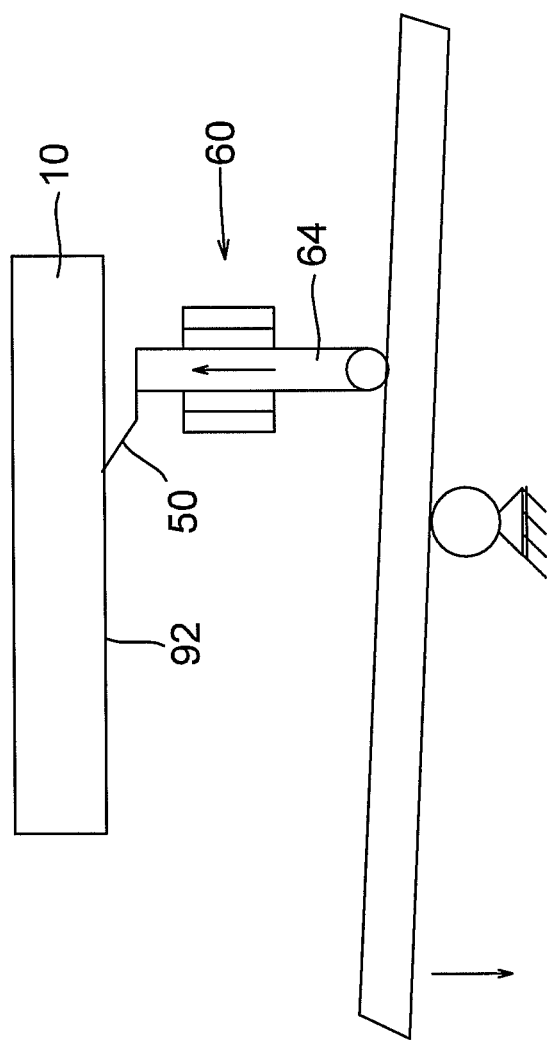
FIG. 13a and FIG. 13b illustrate the diagrams about the working status of the EUV mask and the grounding pin in accordance with the fifth embodiment of the present invention.
Figure 13B:
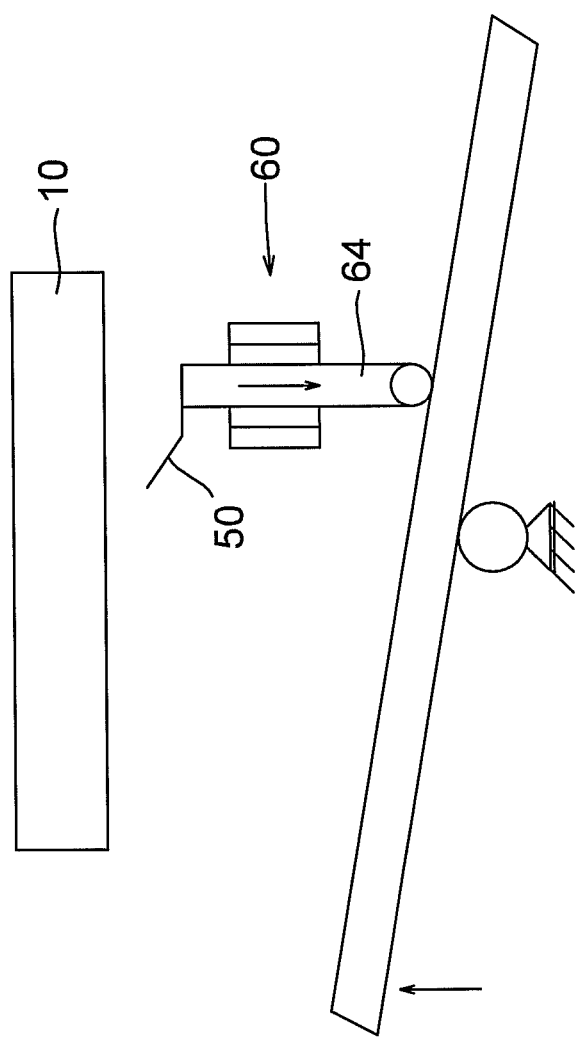

On the other hand, the grounding pin controlling structure 60 described in third embodiment of the present invention may also be applied to the EUV mask 10 with the first conductive layer 90 and the second conductive layer 92 thereon. As shown in FIG. 13*a*, during the inspection of the EUV mask 10, the column 64 moves up and the grounding pin 50 contacts the second conductive layer 92 of the EUV mask 10. After the inspection of the EUV mask 10, as shown in FIG. 13*b*, the column 64 moves down and the grounding pin 50 is far away from the EUV mask 10. The embodiments of the grounding pin controlling structure 60 are described above, and unnecessary details would not be given here.

Figure 14:
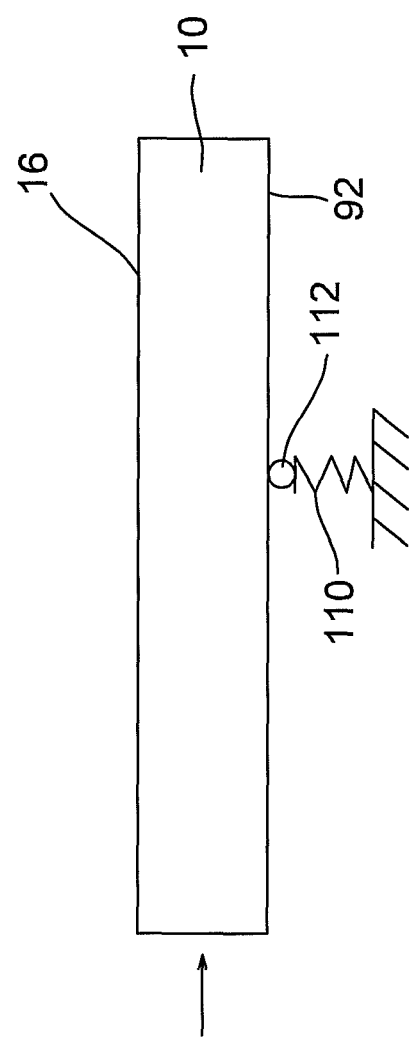
FIG. 14 illustrates the diagrams about the working status of the EUV mask and the grounding pin in accordance with the sixth embodiment of the present invention.

Furthermore, as shown in FIG. 14, the grounding pin may be a spring 110 with a trigger 112 on the top end of the spring 110, and the bottom end of the spring 110 is grounded. When the EUV mask 10 moves to be inspected, the second conductive layer 92 of the EUV mask 10 may contact with the trigger 112 by the weight of the EUV mask 10 to discharge the charge on the reflective surface 16 of the EUV mask 10.

Figure 15A:
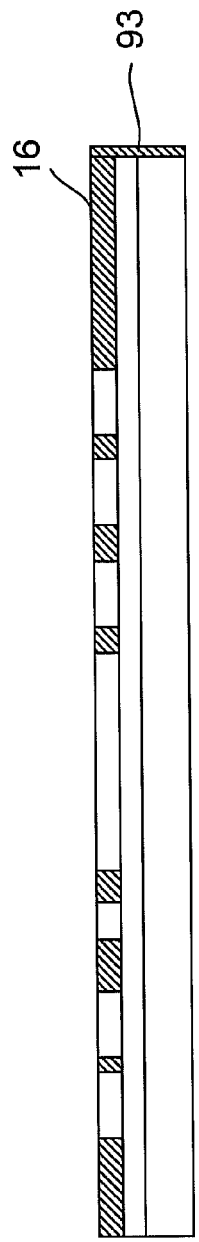
FIG. 15a and FIG. 15b respectively illustrates a cross-sectional view and a vertical view of a configuration of another EUV mask.
Figure 15B:
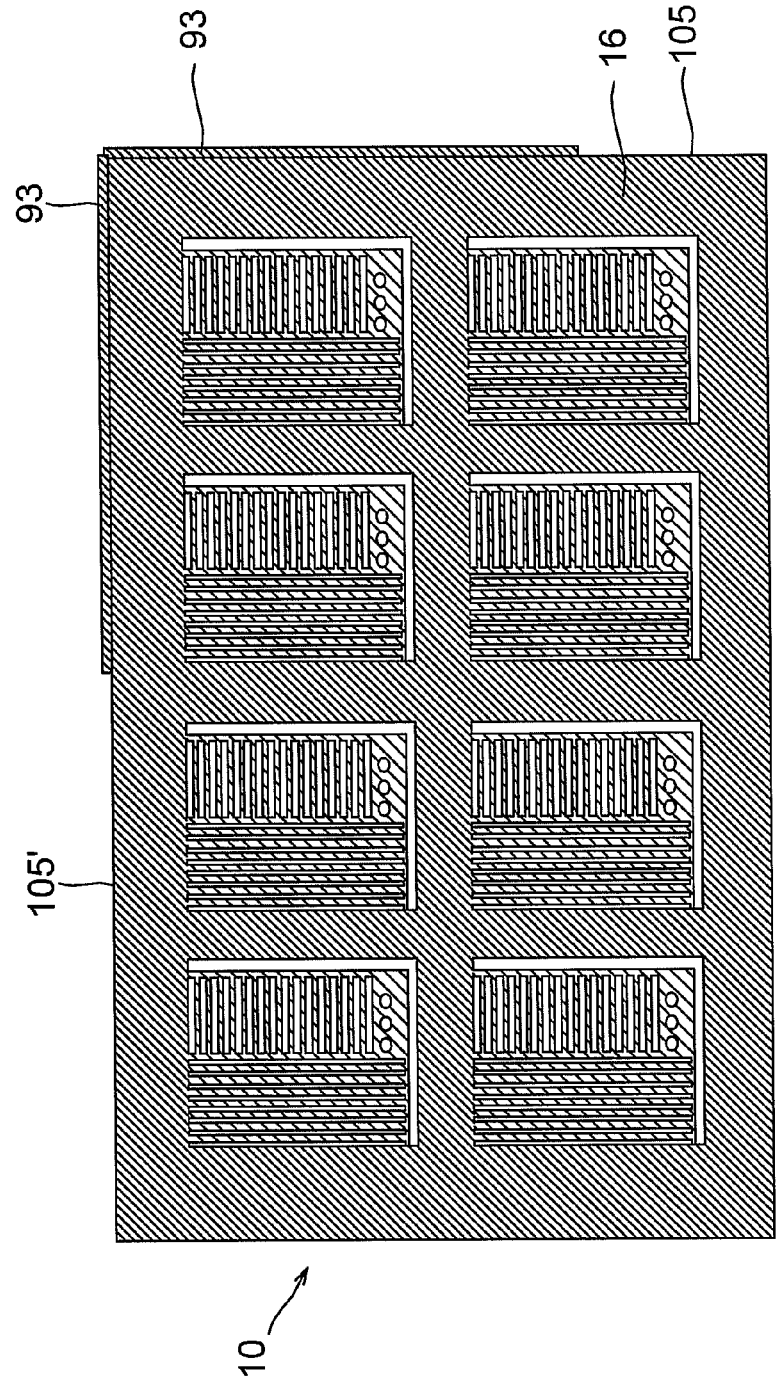
Figure 16:
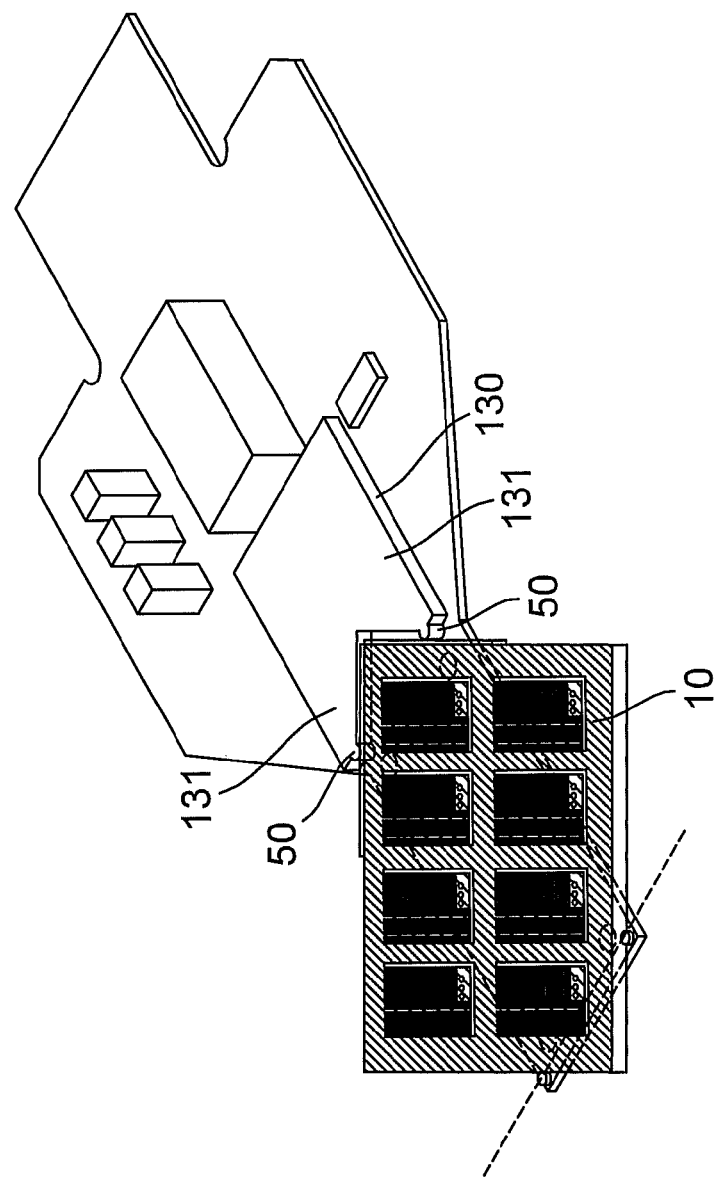
FIG. 16 illustrates a diagram of a conductive holder clamping the EUV mask in accordance with another embodiment of the present invention.

In another embodiment, the grounding pin is used to contact at least one conductive layer on one side of the EUV mask. As shown in FIG. 15*a* and FIG. 15*b*, a conductive layer 93 is formed on one corner of the EUV mask 10, the two adjacent side walls 105, 105', accordingly, and the conductive layer 93 is electrically connected to the reflective surface 16 of the EUV mask 10. The structure for discharging EUV mask includes a conductive holder 130 with the grounding pin 50, as shown in FIG. 16, to clamp the corner of the EUV mask 10, so that the grounding pin 50 may contact with the conductive layer 93. Refer to FIG. 16, two grounding pins 50 are respectively formed on a pair of opposite clamp sections 131 of the conductive holder 130, so that the two grounding pins 50 may contact the conductive layer 13 at two adjacent side walls 105, 105' of the EUV mask 10.

Figure 17:
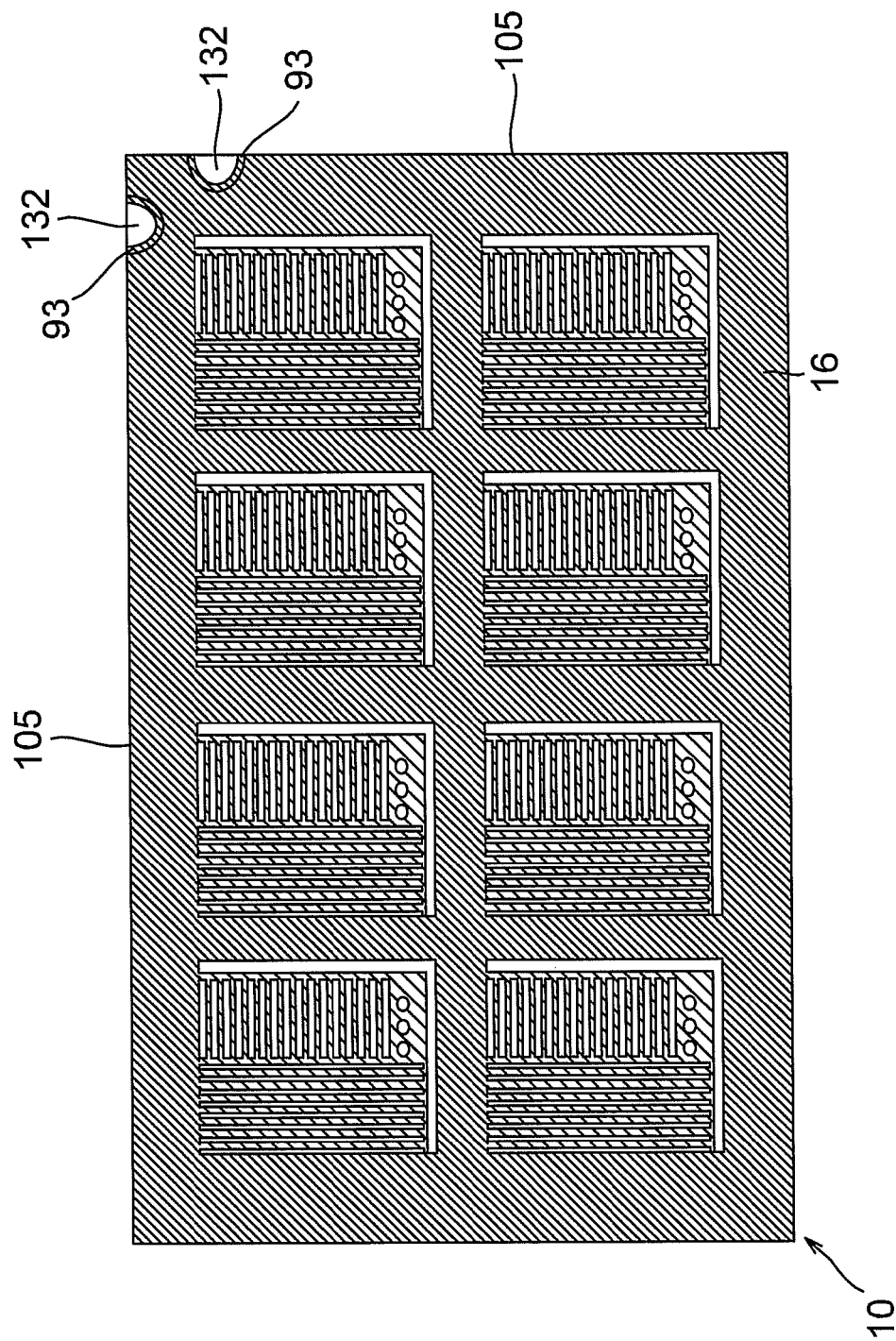
FIG. 17 illustrates a vertical view of a configuration of another EUV mask.

Further, as shown in FIG. 17, two trenches 132 or notches are respectively formed on two adjacent side walls 105, 105' of the EUV mask 10, and a conductive layer 93 formed on the trenches 132 or the notches is electrically connected to the reflective surface 16 of the EUV mask 10. Here, the profile of the trenches 132 or notches may correspond to the grounding pins 50 arranged on the conductive holder 130 as shown in FIG. 16, so that the grounding pin 50 may closely contact the conductive layer 93.

Figure 18:
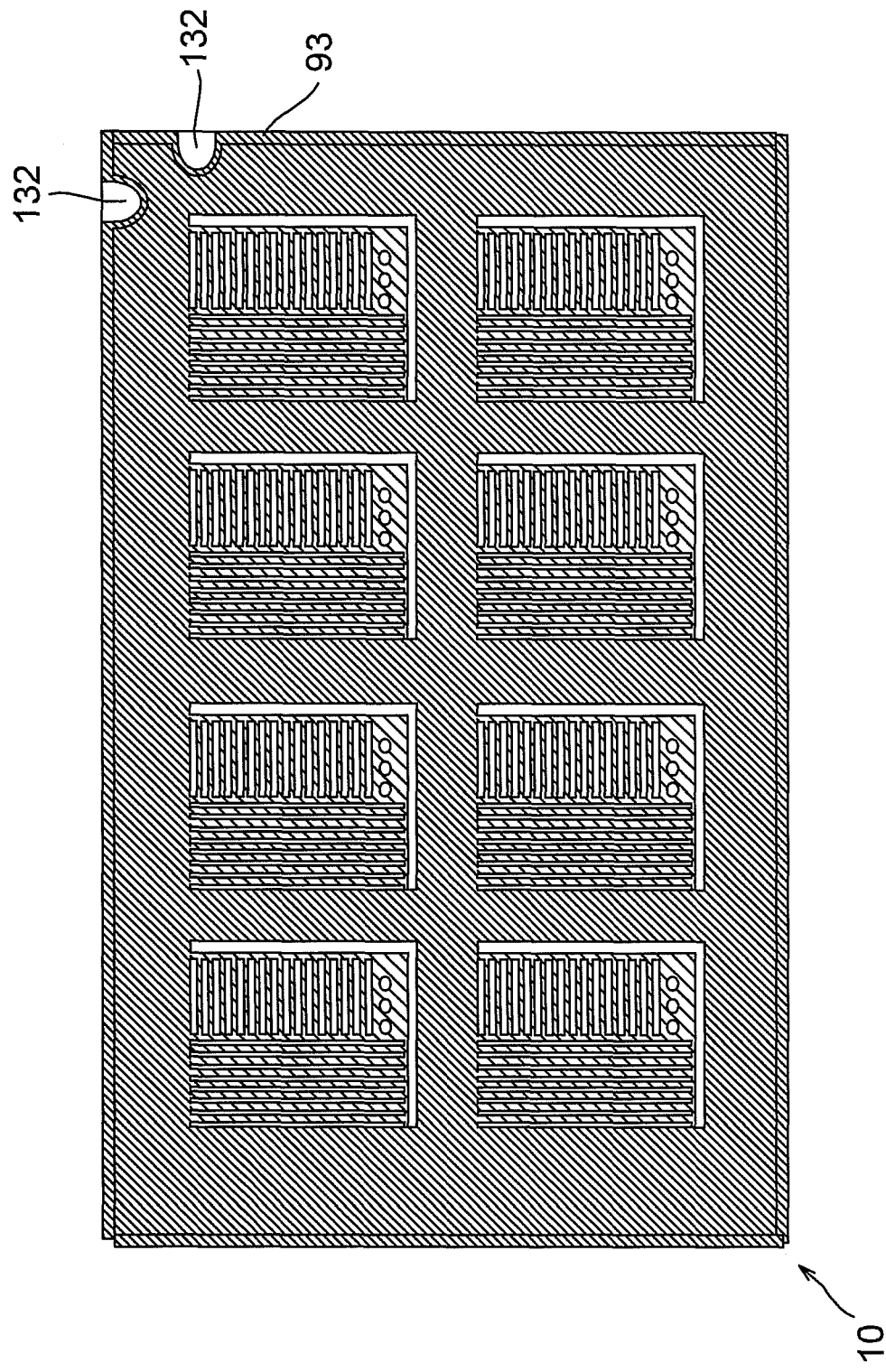
FIG. 18 illustrates a vertical view of a configuration of another EUV mask.

Furthermore, as shown in FIG. 18, the foregoing conductive layer 93 may be formed on the whole side wall, including the trenches 132 or the notches walls, of the EUV mask 10, so that the grounding pin 50 may contact with the conductive layer 93 conveniently. The coated conductive layer 93 may be Al, Cr, Ti, alloy thereof, or non-metal such as carbon. The thickness of the conductive layer 93 may be 0.001 um to 1 mm.

No matter the grounding pin is contacted with the reflective surface, the bottom conductive layer or the side conductive layer, the present invention provides a structure to discharge the EUV mask during inspection by an E-beam inspection tool, so that non accumulated charging is on the EUU mask during E-beam inspecting to enhance the inspection quality.

In the present invention, when applying the foregoing structure to discharge the EUV mask to an electron beam inspection system, the electron beam inspection system for inspecting an EUV mask includes: an electron gun for providing electron beam; a lens for focusing the electron beam on the EUV mask; a detector for receiving signal electron emanating from the EUV mask; and means for discharging the EUV mask during the EUV mask is inspected. The inspection quality of the EUV mask is enhanced by using the electron beam inspection system because the accumulated charging on the EUV mask is grounded.

Although the present invention has been explained in relation to its preferred embodiment, it is to be understood that other modifications and variation can be made without departing the spirit and scope of the invention as hereafter claimed.

What is claimed is:

1. A structure for discharging extreme ultraviolet mask (EUV mask) when said EUV mask is inspected by using a charged particle beam inspection tool, comprising:
   means for conducting charge on an EUV mask in inspecting said EUV mask by using a charged particle beam inspection system;
   a slider with a top surface divided into a flat area and a downward-tilted area;
   an elastic element connecting to a back side of said slider;
   an arm structure comprising a body, a grounding pin on a front end of said body and a prop connecting to said body, wherein said prop contacts said flat area; and
   said EUV mask moving toward a front side of said slider to push said slider back and press said elastic element, so that said prop moves along said top surface of said slider and then contacts said downward-tilted area to make said body of said arm structure tilt and said grounding pin contact said means.

2. A structure for discharging extreme ultraviolet mask (EUV mask) when said EUV mask is inspected by using a charged particle beam inspection tool, comprising:
   means for conducting charge on an EUV mask in inspecting said EUV mask by using a charged particle beam inspection system;
   a gripper unit for fixing said EUV mask in place through rotation of said gripper unit about a first pivot substantially parallel with a first center axis of a first rolling member set at a bottom end of said gripper unit;
   an arm structure comprising a body, a grounding pin on a top end of said body and a second rolling member set at a bottom end of said body, wherein said grounding pin reciprocates to contact said means and leave said EUV mask through rotation of said body about a second pivot substantially parallel with a second center axis of said second rolling member;
   at least one first resilient member and at least one second resilient member each with one end being fixed, and respectively with the other ends being connected to said gripper unit and to said body of said arm structure, for respectively providing a first force to said gripper unit toward a first direction and a second force to said body of said arm structure toward a second direction; and
   a reciprocating member for causing said first rolling member and said second rolling member to rotate, said reciprocating member comprising a fix end and a mobile end pivoting said fixed end, said reciprocating member being in contact with said first rolling member and said second rolling member such that said first rolling member and said second rolling member rolls freely on a surface of said reciprocating member.

3. A structure for discharging extreme ultraviolet mask (EUV mask) when said EUV mask is inspected by using a charged particle beam inspection tool, comprising:
   means for conducting charge on an EUV mask in inspecting said EUV mask by using a charged particle beam inspection system;
   a hollow cylinder having two opposite trenches formed on an inner surface of a side wall of said hollow cylinder, wherein each trench has a lengthwise ditch and an upward-tilted ditch connecting to a top end of said lengthwise ditch;
   a column having two opposite protrusions on an outer surface of said column passing through said hollow cylinder, and said protrusions respectively arranged within said opposite trenches to move along said lengthwise ditch and said upward-tilted ditch;
   a grounding pin arranged on a top surface of said column; and
   a reciprocating member configured for pushing said column to move, wherein when said reciprocating member pushes said column to move down, said column moves down in relative to said hollow cylinder and said grounding pin contacts said means, when said reciprocating member pushes said column to move up continuously in relative to said hollow cylinder, said column moves up straightly and then deflects as said protrusions move along said lengthwise ditch and said upward-tilted ditch, so that said grounding pin is far away from said means.

4. A structure for discharging extreme ultraviolet mask (EUV mask) when said EUV mask is inspected by using a charged particle beam inspection tool, comprising:
   means for conducting charge on an EUV mask in inspecting said EUV mask by using a charged particle beam inspection system;

a hollow cylinder having two opposite trenches passing through a side wall of said hollow cylinder, wherein each trench has a lengthwise ditch passing through said side wall and an upward-tilted ditch passing through said side wall and connecting to a top end of said lengthwise ditch;

a column having two opposite branch structures passing through said hollow cylinder, and said branch structures respectively arranged within said opposite trenches to move along said lengthwise ditch and said titled-upward ditch, wherein every branch structure comprises at least two horizontal rods;

a grounding pin arranged on a top surface of said column; and a reciprocating member configured for pushing said column to move, wherein when said reciprocating member pushes said column to move down, said column moves down in relative to said hollow cylinder and said grounding pin contacts said means, and when said reciprocating member pushes said column to move up continuously in relative to said hollow cylinder, said column moves up straightly and then deflects as said branch structures move along said lengthwise ditch and said upward-tilted ditch, so that said grounding pin is far away from said means.

5. A structure for discharging extreme ultraviolet mask (EUV mask) when said EUV mask is inspected by using a charged particle beam inspection tool, comprising:

a first conductive layer on one side of an EUV mask;

a second conductive layer on a surface opposite to a reflective surface of said EUV mask;

a gripper unit for fixing said EUV mask in place through rotation of said gripper unit about a first pivot substantially parallel with a first center axis of a first rolling member set at a bottom end of said gripper unit;

an arm structure comprising a body, a grounding pin on a top end of said body and a second rolling member set at a bottom end of said body, wherein said grounding pin reciprocates to contact said second conductive layer of said EUV mask and leave said second conductive layer through rotation of said body about a second pivot substantially parallel with a second center axis of said second rolling member, so that charge on said reflective surface of said EUV mask is grounded through said second conductive layer to said grounding pin;

at least one first resilient member and at least one second resilient member each with one end being fixed, and respectively with the other ends being connected to said gripper unit and to said body of said arm structure, for respectively providing a first force to said gripper unit toward a first direction and a second force to said body of said arm structure toward a second direction; and a reciprocating member for causing said first rolling member and said second rolling member to rotate, said reciprocating member comprising a fix end and a mobile end pivoting said fixed end, said reciprocating member being in contact with said first rolling member and said second rolling member such that said first rolling member and said second rolling member rolls freely on a surface of said reciprocating member.

6. A structure for discharging extreme ultraviolet mask (EUV mask) when said EUV mask is inspected by using a charged particle beam inspection tool, comprising:

a first conductive layer on one side of an EUV mask;

a second conductive layer on a surface opposite to a reflective surface of said EUV mask;

a hollow cylinder having two opposite trenches formed on an inner surface of a side wall of said hollow cylinder, wherein each trench has a lengthwise ditch and a downward-tilted ditch connecting to a bottom end of said lengthwise ditch;

a column having two opposite protrusions on an outer surface of said column passing through said hollow cylinder, and said protrusions respectively arranged within said opposite trenches to move along said lengthwise ditch and said downward-tilted ditch;

a grounding pin arranged on a top surface of said column; and a reciprocating member configured for pushing said column to move, wherein when said reciprocating member pushes said column to move up, said column moves up in relative to said hollow cylinder and said grounding pin contacts said second conductive layer, so that charge on said reflective surface of said EUV mask is grounded through said second conductive layer to said grounding pin, when said reciprocating member pushes said column to move down continuously in relative to said hollow cylinder, said column moves down straightly and then deflects as said protrusions move along said lengthwise ditch and said downward-tilted ditch, so that said grounding pin is far away from said second conductive layer.

7. A structure for discharging extreme ultraviolet mask (EUV mask) when said EUV mask is inspected by using a charged particle beam inspection tool, comprising:

a first conductive layer on one side of an EUV mask;

a second conductive layer on a surface opposite to a reflective surface of said EUV mask;

a hollow cylinder having two opposite trenches passing through a side wall of said hollow cylinder, wherein each trench has a lengthwise ditch passing through said side wall and a downward-tilted ditch passing through said side wall and connecting to a bottom end of said lengthwise ditch;

a column having two opposite branch structures passing through said hollow cylinder, and said branch structures respectively arranged within said opposite trenches to move along said lengthwise ditch and said downward-tilted ditch, wherein every branch structure comprises at least two horizontal rods;

a grounding pin arranged on a top surface of said column; and a reciprocating member configured for pushing said column to move, wherein when said reciprocating member pushes said column to move up, said column moves up in relative to said hollow cylinder and said grounding pin contacts said second conductive layer, so that charge on said reflective surface of said EUV mask is grounded through said second conductive layer to said grounding pin, and when said reciprocating member pushes said column to move down continuously in relative to said hollow cylinder, said column moves down straightly and then deflects as said branch structures move along said lengthwise ditch and said downward-tilted ditch, so that said grounding pin is far away from said second conductive layer.

* * * * *